United States Patent [19]
Krumdieck

[11] Patent Number: 5,678,465
[45] Date of Patent: Oct. 21, 1997

[54] TISSUE SLICE THICKNESS MEASURING APPARATUS AND METHOD

[76] Inventor: Carlos Krumdieck, 3408 Wellford Cir., Birmingham, Ala. 35216

[21] Appl. No.: 661,073

[22] Filed: Jun. 10, 1996

[51] Int. Cl.⁶ ................... B26D 1/00; B26D 5/26
[52] U.S. Cl. ............... 83/36; 83/72; 83/74; 83/411.1; 83/411.2; 83/468; 83/915.5
[58] Field of Search ................... 83/34–36, 72, 83/73, 74, 75.5, 76.1, 76.2, 76.7, 76.9, 411.1, 411.4, 468.7, 698, 915.5

[56] References Cited

U.S. PATENT DOCUMENTS

| | | | |
|---|---|---|---|
| 4,377,958 | 3/1983 | Leighton | 83/915.5 |
| 4,484,503 | 11/1984 | Sitte et al. | 83/412 |
| 4,625,608 | 12/1986 | Behme et al. | 83/915.5 |
| 5,148,729 | 9/1992 | Krumdieck | 83/411.1 |
| 5,181,443 | 1/1993 | Sitte et al. | 83/72 |
| 5,414,646 | 5/1995 | Sanders et al. | 364/556 |
| 5,461,953 | 10/1995 | McCormick | 83/915.5 |
| 5,609,083 | 3/1997 | Perrson | 83/73 |

*Primary Examiner*—Maurina T. Rachuba
*Attorney, Agent, or Firm*—Veal & Associates

[57] ABSTRACT

A measuring apparatus for measuring the thickness of slices taken from biological tissue samples by a microtome. The apparatus integrates a digital micrometer, a drive motor, sensing and control circuitry, and a mounting plate, and is designed to be attached to the top of a Krumdieck or similarly designed microtome for measuring the thickness of slices produced. The apparatus is designed so that the spindle of the micrometer is positioned in vertical alignment with the tissue well and plunger of the microtome. The user initiates downward movement of the spindle by depressing a down switch and control circuitry actuates the drive motor to advance the spindle of the micrometer down toward the top of the plunger until the bottom surface of the spindle contacts the plunger. The bottom surface of the spindle is electrically connected to a power source, and the plunger is electrically connected to the control circuitry. Upon contact of the spindle with the plunger, an electrical signal is sent to the control circuitry which instantly disconnects the power to the drive motor and short circuits its leads to create an electro-dynamic brake so that any downward momentum of the spindle and motor are abated. After the spindle is arrested, the user resets the micrometer display to zero. The microtome is then activated to slice away a portion of the tissue sample. The user repeats downward movement procedure of the spindle until again contacting the plunger. After the spindle stops, the micrometer display shows the displacement of the spindle which corresponds to the slice thickness.

35 Claims, 5 Drawing Sheets

TISSUE SLICE THICKNESS MEASURING APPARATUS AND METHOD

FIELD OF THE INVENTION

The present invention relates generally to measuring apparatus used in biological laboratories. More specifically, the present invention relates to measuring apparatus incorporating a micrometer and integrated with a laboratory tissue slicing machine or microtome for determining the thickness of live tissue slices. In greater particularity, the present invention relates to thickness gauges that use control circuitry to advance and retract the spindle of a micrometer relative to a tissue carrier in a microtome to enable accurate measurements of tissue slice thickness, thereby allowing for accurate adjustment of microtome slicing thickness settings to achieve precision in the thickness of slices taken from a tissue sample.

BACKGROUND OF THE INVENTION

Biological live tissue slicing is widely used by laboratories and research institutes for biochemistry, toxicology, pharmacology, neurophysiology, histology, and pathology. One great benefit of live tissue slices is that laboratories can study physiological reactions and occurrences outside the organism without the influence of other biological reactions. Incubation of tissue slices for short periods (hours) was introduced for biochemical studies in 1923 by Otto Warburg. Prolonged incubations (days/weeks) were in practice, not possible until the late 1950's, following the introduction of appropriate tissue culture media and antibacterial and antifungal antibiotics.

To fully realize an effective tissue culture methodology, there must be uniformity between each individual tissue sample for reproducibility among experiments. In the past, the reproducible production of comparable tissue slices from live tissue samples has been extremely difficult. Attempts to produce tissue slices which are uniform in dimension has been met with problems including irreproducibility of slice thickness, contamination of tissue samples and irregular, nonreproducible trauma to the tissue adjacent to the cutting surface.

Two devices which overcome such limitations in reproducibility are the apparatus disclosed by Krumdieck in U.S. Pat. No. 5,148,729 and U.S. patent application No. 08/218,420, herein incorporated by reference. These documents disclose biological tissue slicers which allow an inexperienced technician to produce nearly identical tissue slices in an aseptic environment while minimizing tissue trauma. The invention in '729 included a blade held in a blade holder between two pins while one or more permanent magnets provide a constant downward pull on the blade and blade holder. The design eliminated need for readjustment or tightening which are opportunities for contamination. The reproducibility of tissue slices is increased as vertical "chatter" of the blade decreases. Also, the exposure of the tissue sample to the blade is limited to reduce the extent of trauma to the cut surface of the tissue. The invention in '420 integrated an autoclavable tissue slicer apparatus with a mechanical wash stream pump which is simple and inexpensive to manufacture.

Notwithstanding Krumdieck's improvements, determination of the actual tissue slice thickness remains problematic. Due to variable compressibility of different tissues, the screw adjustment rod (54) of Krumdieck '420 does not provide a sufficiently accurate means of determining the thickness of the slices being cut. Furthermore, the size of the sample and weight of the plunger (31) also affect the thickness of the slice and the screw adjustment rod (54) does not compensate for such variability. The optimal method for experimentation is to measure every time an experiment is conducted the actual thickness of the prepared slice and iteratively adjust the slicer to produce slices of the desired dimensions. In order to improve even further upon the usefulness of the identical tissue slices produced by the Krumdieck devices or similar devices, an accurate gauge and method for measuring the thickness of the resultant tissue slices is needed.

SUMMARY OF THE INVENTION

It is the object of the present invention to provide a measuring device for measuring the thickness of tissue slices produced by a Krumdieck or similar microtomes.

Another object of the current invention is to provide a thickness measuring device for tissue slices that does not touch or in any way damage or contaminate the slice during the measuring process.

A further object is to provide a measuring device that utilizes a digital micrometer electronically controlled for accurate measurement of slice thickness.

Briefly, the invention integrates a digital micrometer, a drive motor, sensing and control circuitry, and a mounting plate. The apparatus is designed to be positioned on the top of a Krumdieck or similarly designed microtome and locked in place. The apparatus is designed so that the spindle of the micrometer is positioned in vertical alignment with the tissue well and plunger of the microtome. The user initiates downward movement of the spindle by depressing a down switch and the control circuitry actuates the drive motor to advance the spindle of the micrometer down toward the top of the plunger until the bottom of the spindle contacts the plunger. Upon contact with the plunger, an electrical signal is sent to the control circuitry which instantaneously interrupts the power to the drive motor and brakes the motor by shorting its power leads so that any downward momentum of the spindle is abated. After the spindle is arrested, the user resets the micrometer display to zero. The microtome is then activated to cut a slice and carry it away and into a collection receptacle. The Krumdieck microtome is designed so that the plunger remains aligned with the spindle after each slicing cycle. The user then again initiates downward movement of the spindle with the down switch, and the control circuitry again advances the spindle until contacting the plunger. The micrometer display shows the displacement of the spindle which corresponds to the slice thickness. With repeated cycles of slicing and measurement, the user can adjust the microtome to achieve a desired precise slice thickness.

Other features and objects and advantages of the present invention will become apparent from a reading of the following description as well as a study of the appended drawings.

BRIEF DESCRIPTION OF THE DRAWINGS

A tissue slice thickness measuring device incorporating the features of the invention is depicted in the attached drawings which form a portion of the disclosure and wherein.

DESCRIPTION OF THE PREFERRED EMBODIMENT

Figures 1, 1A:
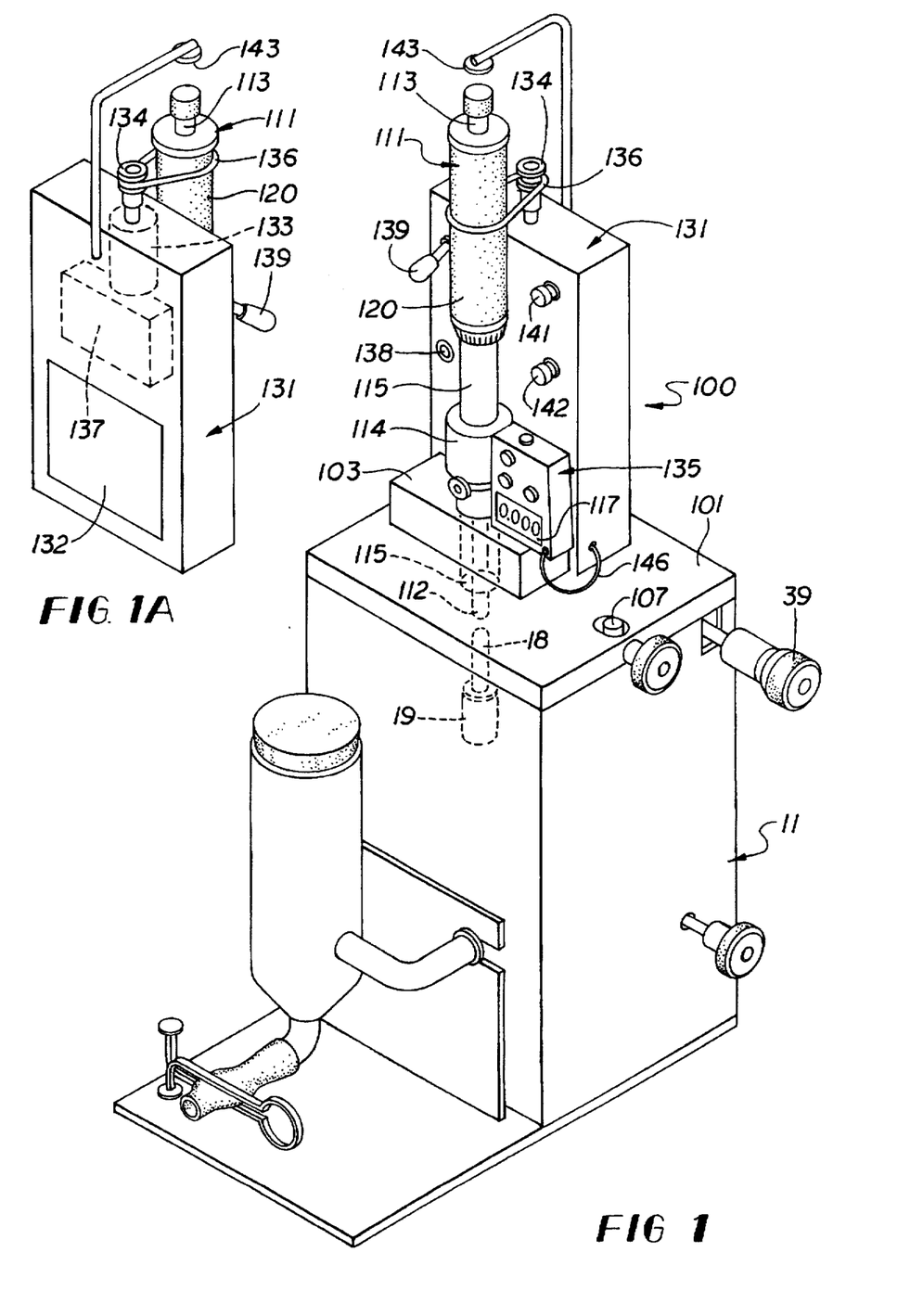
FIG. 1 is a front perspective view of the apparatus mounted on top of a Krumdieck microtome.
FIG. 1A is a rear perspective view of the circuitry enclosure of the invention showing the location of the circuit board and drive motor.

Referring to the drawings for a better understanding of the function and structure of the apparatus, FIG. 1 shows the apparatus clamped in place on the top of a Krumdieck microtome. For convenience and clarity, reference numbers to Krumdieck microtome components are unchanged from the Krumdieck patent no. 5,148,729, herein incorporated by reference, and the components of the current invention are numbered beginning with 100. The main components of the apparatus 100 are mounting base plate 101, a digital micrometer 111 vertically mounted on the base plate, and an electronics case 13 1 containing the control and drive circuitry. The micrometer is a standard digital variety such as manufactured by the Mitutoyo company as is well known in the industry. Aside from critical elements necessary for understanding the operation of the apparatus, a specific discussion of the structure of a micrometer will be omitted as such details would not be warranted or helpful to the artisan. The micrometer spindle 113 extends through the length of the micrometer, passing through a fixed sleeve 115 and a rotatable drive handle 120, which engages the spindle to translate rotational handle movement into linear spindle movement as is well known in the art. The micrometer sleeve 115 is held in place and passes through spindle drum housing 114. Sleeve 115 extends downward from the drum housing through an aperture in an electrically insulating mounting block 103 and is captured by a thrust washer and nut 116, which attaches to the lower end of the sleeve. A brake spring washer (not shown) produces drag to prevent the spindle from rotating freely. Drum housing 114 is affixed to a display housing 135 which supports a liquid crystal display 117 for showing the displacement of the spindle after advancement toward the plunger. Housing 135 also supports a hold button 118, a reset button 119, and a zero/absolute button 121 for zeroing the display in preparation for a slice measurement (See FIG. 3). The insulating mounting block 103 is affixed on top of the base plate 101 with screws 104, 104' over an aperture 102 in the base plate. The bottom surface 112 of the micrometer spindle 113 extends through the housing sleeve 115 into aperture 102 allowing free rotation/vertical displacement of the spindle bottom surface 112 relative to the base plate 101.

Figure 2:
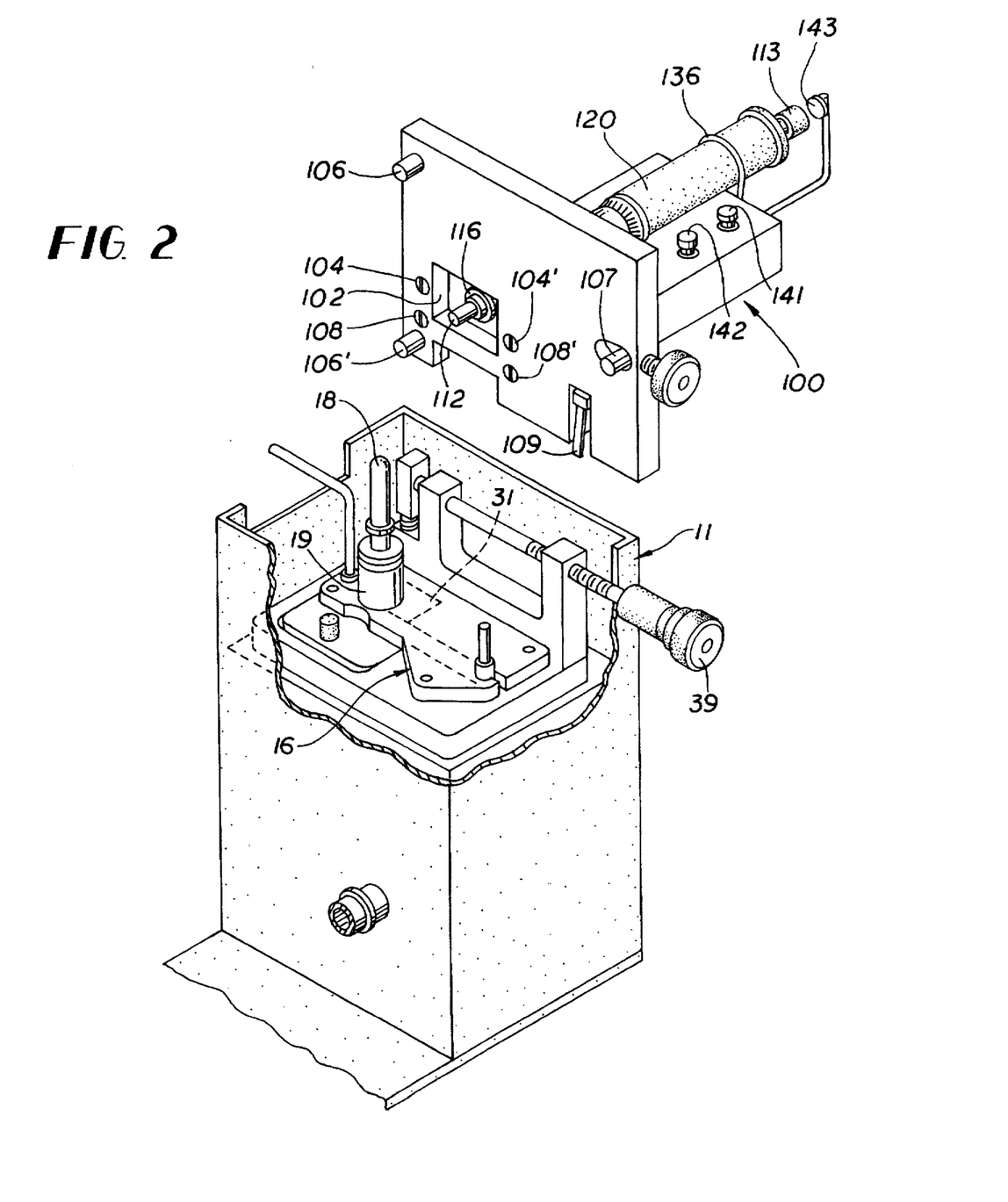
FIG. 2 is an exploded perspective view, partially broken away, showing the underside of the invention.

FIG. 2 shows the apparatus detached from the microtome housing 11 and in perspective to expose the underside of the apparatus. Two depending electrically conducting mounting pins 106, 106' are positioned on plate 101 to match the rectangular dimensions of the inner walls of the microtome housing 11. Once the apparatus 100 is positioned on top of the microtome housing as shown in FIG. 1, a clamping screw and depending pin 107, also electrically conducting, secure the mounting/plate 101 by urging pin 107 outwardly, thereby exerting pressure against the inner side wall of the frame 11 at pins 106 and 107 to prevent movement and to electrically connect it to the microtome. Electronics case 131 is mounted to has plate 101 by screws 108,108'. It should b noted that the positioning of the case may be varied. In addition, interlock switch 109 is positioned in an indentation of the base plate so that the switch closes by engagement with the upper edge of the side wall of the microtome upon proper attainment of the apparatus on the microtome.

FIG. 1A shows a rear perspective view of the electronics case showing the internal components. Circuit control board 132 includes all of the sensing and control circuit for advance, retracting, and braking the spindle 113. The circuit control board actuates drive motor 133 to control the movement of the spindle 113, and the motor transmits movement to the spindle via a concentric pulley 134 and resilient O-ring belt 136 which frictionally engages the pulley and drive belt 136. A rechargable batter 137 provides power to the control board 132 and motor 133, and an eletrical jack 138 allows for an exterior voltage source such as a conventional AC to DC transformer to provide power to the control board and drive motor, and recharge the internal battery 137. A fully charged battery will allow self contained operation of the apparatus for six hours or more.

Referring back to FIG. 1, electronics case 13 1 also includes several user interface switches and the internal circuit board 132 is electrically connected with several contacts. Main power switch 139 provides power to the control board 132 and drive motor 133. Up switch 141 and down switch 142 allow the user to control the movement and direction of the spindle. Top contact switch 143 prevents retraction of the spindle beyond a maximum limit by sending an electrical signal to the control circuitry when the spindle contacts the switch 143, and contact 146 sustains an electrical connection between the conductive spindle body 113 and the control circuitry 132 through display housing 135. Because spindle bottom surface 112 is electrically integral with display housing 135, electrical connectivity with the housing is equivalent to connectivity with the bottom surface 112, and spindle contact with the plunger 18 acts as a maximum down limit contact.

Figure 3:
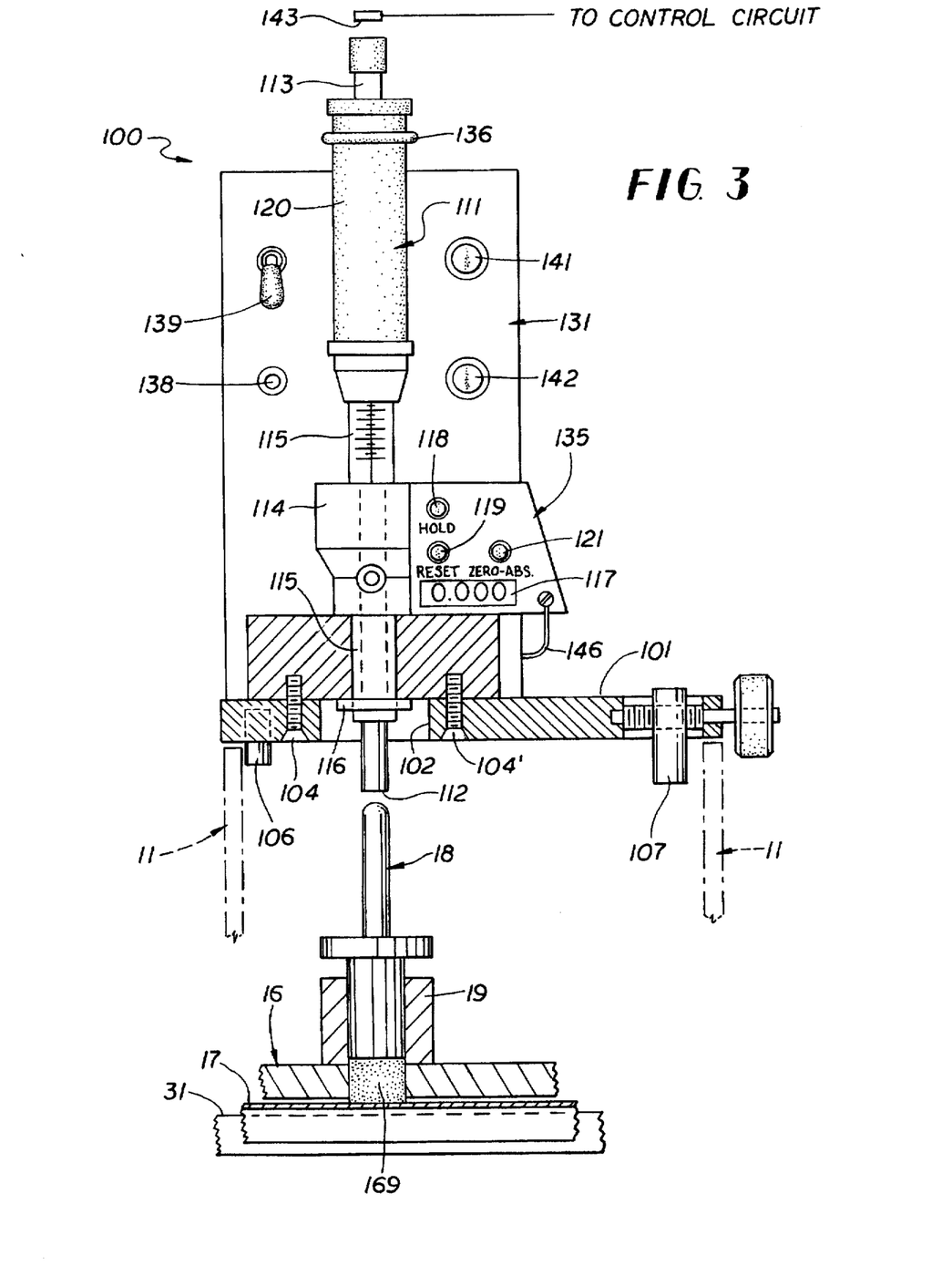
FIG. 3 is a front elevational view of the invention showing the relationship of the plunger bottom end to the critical microtome elements.

FIGS. 2 and 3 disclose the relationship of the spindle bottom to the critical components of the microtome. During a tissue slice cycle, tissue plunger 18 and tissue carrier well 19 assembly move within the microtome housing to effect a tissue slice. However, after the completion of a cycle, the plunger returns to being in vertical alignment with the spindle bottom 112. FIG. 3 shows the spindle bottom in this aligned position. Tissue well 19 encloses a tissue sample 169 which is biased against a vertically adjustable slicing plate 31 and blade 17 by the plunger 18. The tissue well, the enclosed tissue sample, and the plunger are integrated into a tissue holding arm 16 which is movable relative to the plate 31 and blade 17. During a tissue slicing cycle, tissue sample 169 is supported by the adjustable slicer plate 31, and adjustment of the slicer plate 31 by adjustment knob 39 controls the thickness of the sliced away portion of the tissue sample.

Figures 4A, 4B:
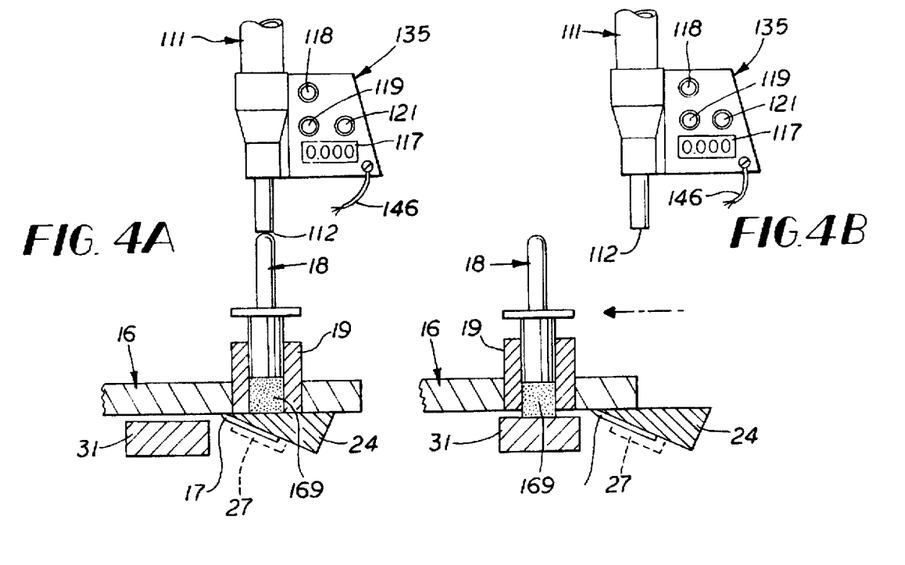
FIGS. 4A–4D are sequenced diagrammatic views of the relationship of the spindle bottom end and the plunger during a tissue slicing cycle.
Figure 4C:
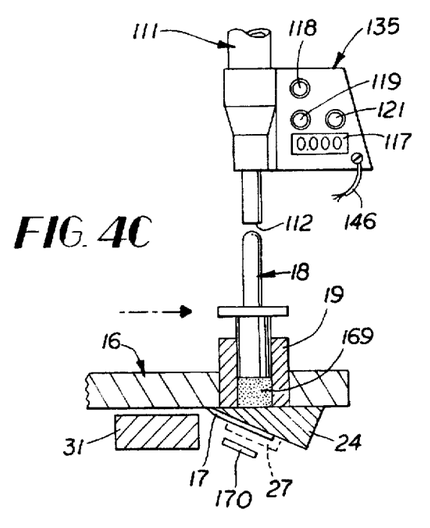
Figure 4D:
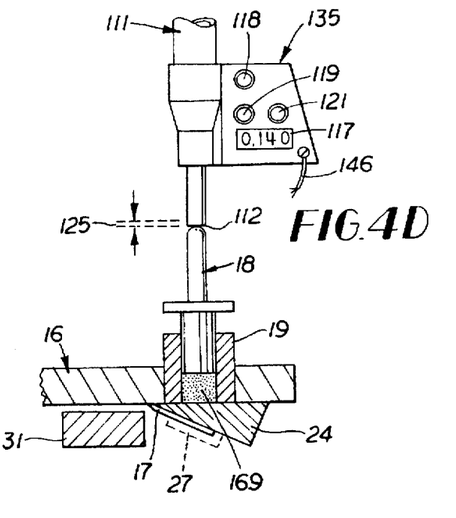
Figure 5:
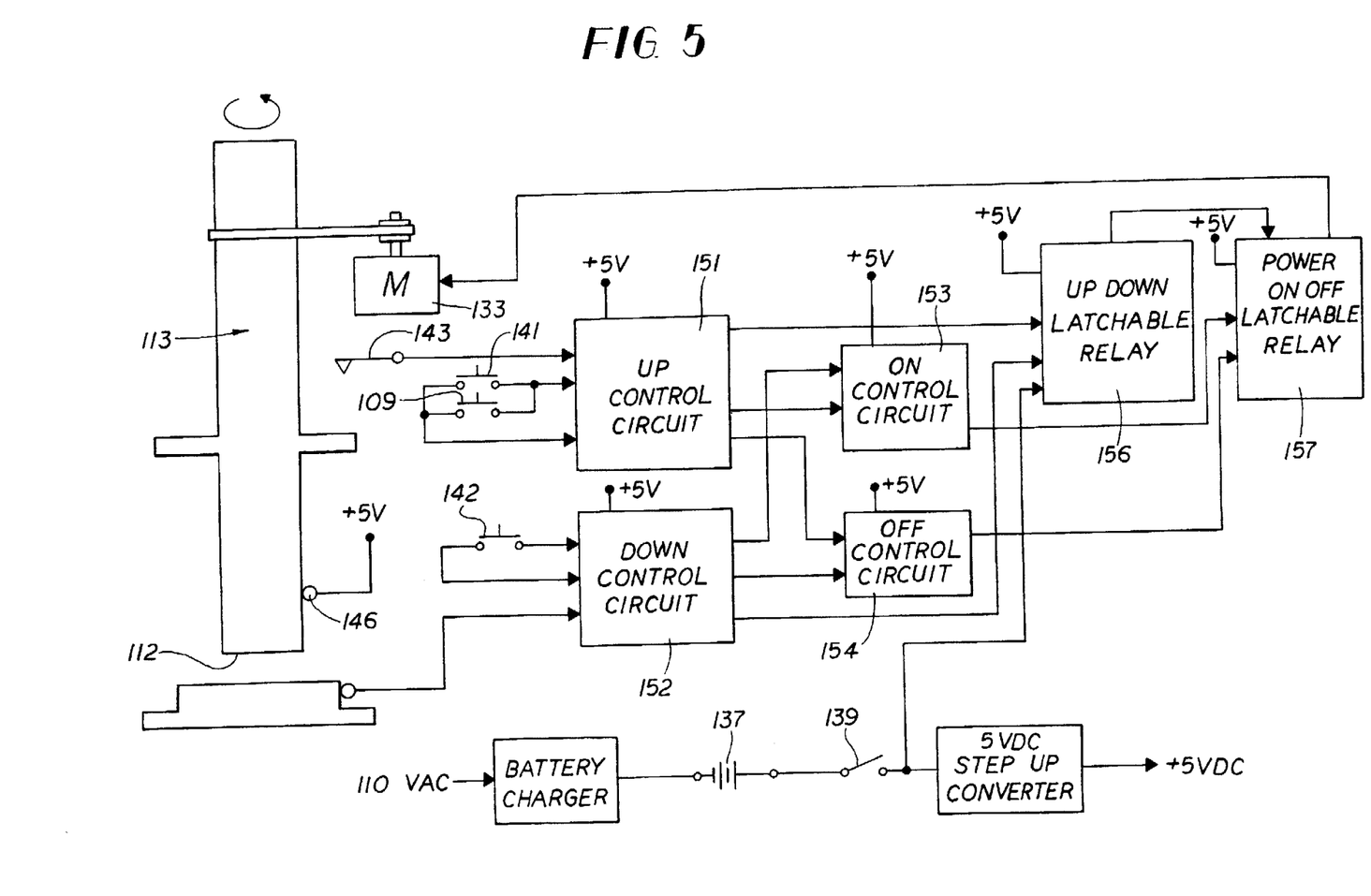
FIG. 5 is a logical block diagram of the control and sensing circuitry of the invention.

To attach the apparatus to the Krumdieck microtome, the user aligns the base mounting plate mounting pins 106, 106' inside the microtome housing 11 walls and clamps the apparatus to the housing to prevent any movement with clamp screw and pin 107. Referring to FIGS. 4A–4D, and FIG. 5, upon connection of the voltage source via main power switch 139, control circuits 151, 152, 153, 154, 156, and 157 are initialized to a known state. FIG. 4A shows the zeroing position for the tissue sample 169, well 19, and plunger 18. The control circuits may be programmable logic circuits or analog switch circuits. The user presses the down switch 142 to lower the micrometer spindle 113 and bottom 112 toward the plunger 18. Upon pressing the down switch 142, down control circuit 152 causes power relay 157 to latch in a down power polarity orientation via on control circuit 153 and programmable up/down latchable relay 156. In response to the application of power from power relay 157, motor 133 rotates spindle 113 with O-ring belt 136. The spindle advances until the spindle bottom surface 112 contacts the plunger. Upon contact, a circuit is closed between contact 146, the micrometer, the plunger 18, and the down control circuitry 152. In response, down control circuit 152 sends a signal to the off control circuit 154 and to the power on/off latchable relay 157 to disconnect the power to motor 133 and short the leads of motor 133. This acts as a dynamic brake to prevent coasting of the motor and spindle due to inertia, thereby preventing compression of the tissue sample from continued advancement of the spindle bottom 112. Due to the dynamic braking circuit, inertial errors are made negligible. Next, the user depresses zero switch 121 to set the zero displacement point in the micrometer. The user then activates the Krumdieck slicer which moves the tissue holding arm 16, tissue well 19 containing the tissue sample 169, and the plunger 18 (the movement direction is indicated by the arrow in FIG. 4B) onto the adjustable slicer plate 31. FIG. 4B shows the tissue sample resting on the plate 31 which has been adjusted with knob 39 to obtain a desired thickness. The slicer then moves the sample, well, arm, and plunger assembly back toward the reciprocally moving blade assembly composed of a slicing blade 17, blade holder 27, and wedge 24. As the sample moves over the surface of the slicer plate 31 and into the blade 17, a thin slice 170 of the sample falls below the blade 17 into a retrieval receptacle containing a sterile buffer fluid (see FIG. 4C). The user again advances the spindle 113 and bottom 112 toward the plunger by depressing the down switch 142. As described above, the control circuitry actuates the motor and advances the spindle until it contacts the plunger at which point the spindle is again dynamically braked. Due to the design of the microtome and the orientation of the spindle relative to the plunger, the plunger is always aligned with the micrometer bottom after each slicing cycle. As shown in FIG. 4D, after the spindle contacts the plunger, the micrometer display indicates the displacement 125 of the spindle advancement which corresponds to the thickness of the slice. Iterative slicing cycles in combination with measurement of the slice thickness allows for adjustment of the microtome to achieve a desired precise slice thickness.

After a succession of slicing cycles, the tissue sample 169 may be totally consumed. To insert a new sample, the locking clamp screw 107 is loosened and the apparatus lifted from the microtome for access to the plunger and tissue well. Interlock switch 109 facilitates this process by automatically initiating upward movement of the spindle away from the plunger upon removal of the apparatus from the microtome. Interlock switch 109 signals up control circuit 151 to actuate power relay 157 via latchable relay 156 for proper biasing of the power to the motor. Power will be supplied to motor 133 until spindle has reached an upper most travel position at which time spindle body 113 contacts top contact 143. Alternatively, up switch 141 may be actuated to signal up control circuit 151 and initiate upward movement of the spindle. Contact of the spindle body with contact 143 signals up control 151 to discontinue power to the motor 133 thereby arresting movement of the spindle. The speed of the motor going up is approximately twice as fast as going down. This is done to avoid unnecessary delays when changing samples due to having to wait for the spindle to complete its upward travel in order to make room for the raised plunger with a new sample. The spring washer internal to the micrometer prevents movement of the spindle when power is not provided to the motor.

Once a new tissue sample has been placed in the tissue well and the apparatus has been reattached to the microtome, the user advances the spindle by pressing the down button 142. To increase the speed of the downward travel, the user can manually turn the spindle by hand, which will cause the O-ring belt to slip without damaging the motor.

While I have shown my invention in one form, it will be obvious to those skilled in the art that it is not so limited but is susceptible of various changes and modifications without departing from the spirit thereof Furthermore, while I have shown the invention in combination with my Krumdieck microtome, it is contemplated that the invention is adaptable to fit other microtomes with similar critical components without departing from the structure herein claimed and disclosed.

Having set forth the nature of the invention, what is claimed is:

1. A measuring apparatus used in combination with a microtome for iteratively slicing a tissue sample into a plurality of uniform tissue slices, said microtome having a slicing plate, a reciprocally movable blade assembly mounted at a predetermined height above said slicing plate, a tissue carrier assembly mounted for iterative movement across said blade assembly, said tissue carrier assembly including a receptacle for holding said tissue sample, and plunger means carried within said receptacle for biasing said tissue sample against said slicing plate, in combination with a micrometer including a variable height spindle having a bottom surface and a human sensible display for showing displacement of said spindle, comprising:

a. movement means for controllably advancing and retracting said spindle relative to said plunger means;

b. control means responsive to user input for regulating said movement means to control movement of said spindle; and c. a mounting assembly for mounting said micrometer, said movement means, and said control means on said microtome.

2. A measuring apparatus as recited in claim 1, wherein said movement means comprises:

a. a motor having an output shaft; and b. transmission means for transmitting rotation of said shaft to said spindle for rotation thereof.

3. A measuring apparatus as recited in claim 2, wherein said motor includes a concentric pulley attached to said output shaft for concomitant rotation thereon, and wherein said transmission comprises a belt for translating rotation from said pulley to said spindle.

4. A measuring apparatus as recited in claim 1, further comprising sensing means for detecting contact of said bottom surface with said plunger means and outputting a signal to said control means responsive to such contact, wherein said control means interacts with said move mere means in response to said signal to decelerate said spindle.

5. A measuring apparatus as recited in claim 4, wherein said control means comprises:

a. voltage means for receiving and applying a voltage source to said control means;

b. electrical switch means responsive to said sensing means;

c. user interface means operationally connected to said electrical switch means; and, d. power control means responsive to said electrical switch means for selectively applying said voltage to said movement means.

6. A measuring apparatus as recited in claim 5, wherein said electrical switch means comprises:
   a. an up control switch circuit;
   b. a down control switch circuit; and,
   c. means for connecting said up and down control switch circuits to said power control means.

7. A measuring apparatus as recited in claim 6, wherein said control means includes a top contact signal means electrically connected to said up control switch circuit for stopping movement of said spindle upon reaching a preset uppermost travel position.

8. A measuring apparatus as recited in claim 5, wherein said control means includes an interlock signal means electrically connected to said electrical switch means for initiating up movement of said spindle upon detachment of said measuring apparatus from said microtome.

9. A measuring apparatus as recited in claim 8, wherein said sensing means comprises:
   a. means for electrically connecting said electrical switch means to said bottom surface; and,
   b. means for electrically connecting said plunger means to said voltage means so that an electrical circuit is closed upon said bottom surface, contacting said plunger means.

10. A measuring apparatus as recited in claim 5, wherein said voltage means includes a rechargeable voltage source and external connector means for recharging said source.

11. A measuring apparatus as recited in claim 5, wherein said power control means comprises:
    a. a first latchable relay for actuating said movement means, said first relay including programmable output polarity means; and
    b. a second latchable relay responsive to said electrical switch means and connected to said first latchable relay for setting said output polarity means.

12. A measuring apparatus as recited in claim 11, wherein said electrical switch means includes brake circuit means responsive to said signal from said sensing means for disconnecting said voltage source from said movement means and simultaneously shorting input leads to said movement means so that said movement means arrests movement of said spindle to insure accurate measurement.

13. A measuring apparatus as recited in claim 12, wherein said sensing means comprises:
    a. means for electrically connecting said electrical switch means to said bottom surface; and,
    b. means for electrically connecting said plunger means to said voltage means so that an electrical circuit is closed upon said bottom surface contacting said plunger means.

14. A measuring apparatus as recited in claim 13, wherein said means for electrically connecting said plunger means to said voltage means comprises:
    a. wherein said mounting assembly is electrically conductive;
    b. wherein said plunger means is electrically conductive;
    c. wherein said microtome includes an electrically conductive frame;
    d. means for electrically connecting said mounting assembly to said voltage means;
    e. means for electrically connecting said mounting assembly to said frame; and
    f. means for electrically connecting said plunger means to said frame.

15. A measuring apparatus as recited in claim 5, wherein said sensing means comprises:
    a. means for electrically connecting said electrical switch means to said bottom surface; and,
    b. means for electrically connecting said plunger means to said voltage means so that an electrical circuit is closed upon said bottom surface contacting said plunger means.

16. A measuring apparatus as recited in claim 5, wherein said user interface means comprises:
    a. a main power switch for connecting said voltage means to said control means;
    b. a down switch electrically connected to said electrical switch means for advancing said bottom surface of said spindle toward said plunger means; and,
    c. an up switch electrically connected to said electrical switch means for retracting said bottom surface of said spindle from said plunger means.

17. A measuring apparatus used in combination with a microtome for iteratively slicing a tissue sample into a plurality of uniform tissue slices, said microtome including tissue carrier means for holding said tissue sample, a slicing plane, slicing means for slicing away a portion of said tissue sample, said slicing means positioned at a predetermined distance away from said slicing plane, and biasing means for biasing said tissue sample against said slicing plane, in combination with a micrometer including a variable height spindle having a bottom surface and a human sensible display for showing displacement of said spindle, comprising:
    a. movement means for controllably advancing and retracting said spindle relative to said biasing means;
    b. control means responsive to user input for regulating said movement means to control movement of said spindle; and
    c. a mounting assembly for mounting said micrometer, said movement means, and said control means on said microtome.

18. A measuring apparatus as recited in claim 17, wherein said movement means comprises:
    a. a motor having an output shaft; and
    b. transmission means for transmitting rotation of said shaft to said spindle for rotation thereof.

19. A measuring apparatus as recited in claim 18, wherein said motor includes a concentric pulley attached to said output shaft for concomitant rotation thereon, and wherein said transmission comprises a belt for translating rotation from said pulley to said spindle.

20. A measuring apparatus as recited in claim 17, further comprising sensing means for detecting contact of said bottom surface with said biasing means and outputting a signal responsive to such contact, wherein said control means interactes with said movement means in response to said signal to decelerate said spindle.

21. A measuring apparatus as recited in claim 20, wherein said control means comprises:
    a. voltage means for receiving and applying a voltage source to said control means;
    b. electrical switch means responsive to said sensing means;
    c. user interface means operationally connected to said electrical switch means; and,
    d. power control means responsive to said electrical switch means for selectively applying said voltage to said movement means.

22. A measuring apparatus as recited in claim 21, wherein said electrical switch means comprises:
   a. an up control switch circuit;
   b. a down control switch circuit; and,
   c. means for connecting said up and down control switch circuits to said power control means.

23. A measuring apparatus as recited in claim 22, wherein said control means includes a top contact signal means electrically connected to said up control switch circuit for stopping movement of said spindle upon reaching a preset uppermost travel position.

24. A measuring apparatus as recited in claim 21, wherein said control means includes an interlock signal means electrically connected to said electrical switch means for initiating up movement of said spindle upon detachment of said measuring apparatus from said microtome.

25. A measuring apparatus as recited in claim 24, wherein said sensing means comprises:
   a. means for electrically connecting said electrical switch means to said bottom surface; and,
   b. means for electrically connecting said biasing means to said voltage means so that an electrical circuit is closed upon said bottom surface contacting said biasing means.

26. A measuring apparatus as recited in claim 21, wherein said voltage means includes a rechargeable voltage source and external connector means for recharging said source.

27. A measuring apparatus as recited in claim 21, wherein said power control means comprises:
   a. a first latchable relay for actuating said movement means, said first relay including output polarity means; and
   b. a second latchable relay responsive to said electrical switch means and connected to said first latchable relay for setting said output polarity means.

28. A measuring apparatus as recited in claim 27, wherein said electrical switch means includes brake circuit means responsive to said signal from said sensing means for disconnecting said voltage source from said movement means and simultaneously shorting input leads to said movement means so that said movement means arrests movement of said spindle to insure accurate measurement.

29. A measuring apparatus as recited in claim 28, wherein said sensing means comprises:
   a. means for electrically connecting said electrical switch means to said bottom surface; and,
   b. means for electrically connecting said biasing means to said voltage means so that an electrical circuit is closed upon said bottom surface contacting said biasing means.

30. A measuring apparatus as recited in claim 29, wherein said means for electrically connecting said biasing means to said voltage means comprises:
   a. wherein said mounting assembly is electrically conductive;
   b. wherein said biasing means is electrically conductive;
   c. wherein said microtome includes an electrically conductive frame;
   d. means for electrically connecting said mounting assembly to said voltage means;
   e. means for electrically connecting said mounting assembly to said frame; and
   f. means for electrically connecting said biasing means to said frame.

31. A measuring apparatus as recited in claim 21, wherein said sensing means comprises:
   a. means for electrically connecting said electrical switch means to said bottom surface; and,
   b. means for electrically connecting said biasing means to said voltage means so that an electrical circuit is closed upon said bottom surface contacting said biasing means.

32. A measuring apparatus as recited in claim 21, wherein said user interface means comprises:
   a. a main power switch for connecting said voltage means to said control means;
   b. a down switch electrically connected to said electrical switch means for advancing said bottom surface of said spindle toward said biasing means; and,
   c. an up switch electrically connected to said electrical switch means for retracting said bottom surface of said spindle from said biasing means.

33. A method for measuring the thickness of a tissue sample slice used in combination with a microtome for iteratively slicing a tissue sample into a plurality of uniform tissue slices, said microtome having a slicing plate, a reciprocally movable blade assembly mounted at a predetermined height above said slicing plate, a tissue carrier assembly mounted for iterative movement across said blade assembly, said tissue carrier assembly including a receptacle for holding said tissue sample, and plunger means carried within said receptacle for biasing said tissue sample against said slicing plate, in combination with a micrometer including a variable height spindle having a bottom surface and a human sensible display for showing displacement of said spindle, the steps comprising:
   a. loading a tissue sample in said tissue carrier;
   b. biasing said tissue sample against said blade assembly with said plunger means;
   c. advancing said spindle toward said plunger means;
   d. braking said advancement of said spindle upon contact with said plunger means;
   e. slicing away a portion of said tissue sample by moving said tissue carrier assembly onto said slicing plate and then moving said tissue carrier assembly back over said blade assembly;
   f. again advancing said spindle toward said plunger means;
   g. again braking said advancement of said spindle upon contact with said plunger means; and,
   h. reading a displacement of said spindle on said display to determine a thickness of said sliced away portion.

34. The method according to claim 33, including the additional step of resetting said display on said micrometer prior to advancing said spindle.

35. The method according to claim 33, wherein each said braking step comprises:
   a. receiving a signal from said plunger means indicating contact with said bottom surface; and,
   b. applying a force to said spindle to abate coasting advancement of said spindle.

* * * * *